(12) United States Patent
Khawaji et al.

(10) Patent No.: US 11,840,493 B2
(45) Date of Patent: Dec. 12, 2023

(54) ANTIFOULING OLIGOMERIZATION CATALYST SYSTEMS

(71) Applicants: Saudi Arabian Oil Company, Dhahran (SA); Sumitomo Chemical Company, Limited, Tokyo (JP)

(72) Inventors: Motaz Khawaji, Thuwal (SA); Hussain Al Yami, Thuwal (SA); Sohel Shaikh, Dhahran (SA); Wei Xu, Dhahran (SA); Kenji Sogo, Kuranamidai (JP)

(73) Assignees: Saudi Arabian Oil Company, Dhahran (SA); Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 17/383,725

(22) Filed: Jul. 23, 2021

(65) Prior Publication Data

US 2021/0347712 A1    Nov. 11, 2021

Related U.S. Application Data

(62) Division of application No. 15/393,865, filed on Dec. 29, 2016, now Pat. No. 11,104,621.

(60) Provisional application No. 62/275,932, filed on Jan. 7, 2016.

(51) Int. Cl.
| | |
|---|---|
| *B01J 31/00* | (2006.01) |
| *C07C 2/32* | (2006.01) |
| *B01J 31/12* | (2006.01) |
| *B01J 31/02* | (2006.01) |
| *C07C 2/30* | (2006.01) |
| *B01J 31/14* | (2006.01) |
| *B01J 31/22* | (2006.01) |
| *B01J 31/06* | (2006.01) |

(52) U.S. Cl.
CPC ............ *C07C 2/32* (2013.01); *B01J 31/0212* (2013.01); *B01J 31/123* (2013.01); *B01J 31/143* (2013.01); *B01J 31/2208* (2013.01); *C07C 2/30* (2013.01); *B01J 31/068* (2013.01); *B01J 2231/20* (2013.01); *B01J 2531/46* (2013.01); *C07C 2531/14* (2013.01); *C07C 2531/22* (2013.01)

(58) Field of Classification Search
None
See application file for complete search history.

(56) References Cited

U.S. PATENT DOCUMENTS

| | | |
|---|---|---|
| 2,738,151 A | 3/1956 | Herzog |
| 3,061,602 A | 10/1962 | Duck et al. |
| 3,686,350 A | 8/1972 | Yamada et al. |
| 4,242,531 A | 12/1980 | Carter |
| 4,484,016 A | 11/1984 | Maschmeyer et al. |
| 4,528,415 A | 7/1985 | Knudsen |
| 4,532,370 A | 7/1985 | Le' Quan et al. |
| 4,538,018 A | 8/1985 | Carter |
| 4,606,854 A | 8/1986 | Ozawa et al. |
| 4,615,998 A | 10/1986 | Le' Quan et al. |
| 5,292,837 A | 3/1994 | Heinrich et al. |
| 5,376,706 A | 12/1994 | Barsotti et al. |
| 5,494,171 A | 2/1996 | Kazamoto et al. |
| 5,728,912 A | 3/1998 | Saqualain Haider Rizvi et al. |
| 5,792,895 A | 8/1998 | Commereuc et al. |
| 5,811,618 A | 9/1998 | Wu |
| 5,856,612 A | 1/1999 | Araki et al. |
| 5,877,376 A | 3/1999 | Commereuc et al. |
| 6,184,428 B1 | 2/2001 | Zahoor et al. |
| 6,757,975 B1 | 7/2004 | Liu |
| 7,122,497 B1 | 10/2006 | Nagy et al. |
| 7,157,532 B2 | 1/2007 | Payer et al. |
| 7,329,635 B2 | 2/2008 | Dickakian et al. |
| 7,361,623 B2 | 4/2008 | Dixon et al. |
| 7,638,597 B2 | 12/2009 | Therton et al. |
| 7,919,569 B2 | 4/2011 | Xu et al. |
| 7,964,763 B2 | 6/2011 | Dixon et al. |
| 8,227,653 B2 | 7/2012 | Weber et al. |
| 8,252,871 B2 | 8/2012 | Aliyev et al. |

(Continued)

FOREIGN PATENT DOCUMENTS

| | | |
|---|---|---|
| CN | 101189270 A | 5/2008 |
| CN | 102807632 A | 12/2012 |

(Continued)

OTHER PUBLICATIONS

Office Action dated Feb. 25, 2021 pertaining to U.S. Appl. No. 15/181,923, filed Jun. 14, 2016, 36 pgs.

(Continued)

*Primary Examiner* — Yun Qian

(74) *Attorney, Agent, or Firm* — DINSMORE & SHOHL LLP

(57) ABSTRACT

According to one embodiment, a catalyst system that reduces polymeric fouling may comprise at least one titanate compound, at least one aluminum compound, and at least one antifouling agent or a derivative thereof. The antifouling agent may comprise a structure comprising a central aluminum molecule bound to an R1 group, bound to an R2 group, and bound to an R3 group. One or more of the chemical groups R1, R2, and R3 may be antifouling groups comprising the structure —O(($CH_2$)$_n$O)$_m$R4, where n is an integer from 1 to 20, m is an integer from 1 to 100, and R4 is a hydrocarbyl group. The chemical groups R1, R2, or R3 that do not comprise the antifouling group, if any, may be hydrocarbyl groups.

20 Claims, No Drawings

(56) References Cited

U.S. PATENT DOCUMENTS

| | | | |
|---|---|---|---|
| 10,280,125 | B2 | 5/2019 | Sogo et al. |
| 2003/0109766 | A1 | 6/2003 | Commereuc et al. |
| 2007/0027276 | A1 | 2/2007 | Cann et al. |
| 2013/0123443 | A1 | 5/2013 | Siraux et al. |
| 2013/0303817 | A1 | 11/2013 | Shaik et al. |
| 2014/0088331 | A1 | 3/2014 | Axens |
| 2014/0250835 | A1 | 9/2014 | Prabhu et al. |
| 2015/0141605 | A1 | 5/2015 | Bradin |
| 2016/0367977 | A1* | 12/2016 | Shaikh ............... B01J 31/04 |
| 2017/0197892 | A1 | 7/2017 | Khawaji et al. |
| 2017/0274356 | A1 | 9/2017 | Cann et al. |

FOREIGN PATENT DOCUMENTS

| | | |
|---|---|---|
| CN | 103665201 A | 3/2014 |
| CN | 103124149 A | 4/2014 |
| CN | 107778388 A | 3/2018 |
| EP | 0135441 A1 | 3/1985 |
| EP | 0181954 A1 | 5/1986 |
| EP | 0221206 A1 | 5/1987 |
| EP | 0352856 A1 | 1/1990 |
| EP | 2738151 A1 | 6/2014 |
| JP | H02-1990-088529 | 3/1990 |
| RU | 2561921 C1 | 9/2015 |
| WO | 2012013805 A1 | 2/2012 |
| WO | 2013154446 A1 | 10/2013 |
| WO | 2015087303 A2 | 6/2015 |
| WO | 2015087304 A2 | 6/2015 |
| WO | 2015087305 A2 | 6/2015 |
| WO | 2015118462 A1 | 8/2015 |

OTHER PUBLICATIONS

Office Action dated Jan. 6, 2021 pertaining to Japanese Patent Application No. 2018-535418.
International Search Report and Written Opinion dated Mar. 18, 2021 pertaining to International application No. PCT/US2020/059974 filed Nov. 11, 2020, 13 pgs.
Karin et al. "Removal of Trace Elemental Impurities from Polyethylene by Nitric Acid", Analytical Chemistry, vol. 47, No. 13, Nov. 1975, 4 pgs.
Office Action pertaining to RU2018128919 dated Feb. 27, 2020, 10 pgs.
Notice of Allowance and Fee(s) Due dated Sep. 10, 2020 pertaining to U.S. Appl. No. 16/134,207, filed Sep. 18, 2018, 21 pgs.
U.S. Office Action dated Aug. 20, 2020 pertaining to U.S. Appl. No. 15/181,923, filed Jun. 14, 2016, 23 pgs.
Office Action dated Mar. 30, 2020 pertaining to U.S. Appl. No. 16/134,207, filed Sep. 18, 2018, 52 pgs.
Office Action dated Jul. 8, 2020 pertaining to Japanese Patent Application No. 2017-565808.
Office Action dated Aug. 10, 2020 pertaining to Singapore Patent Application No. 11201805653U.
Examination Report pertaining to India Application No. 201837025980 dated Apr. 27, 2020, 6 pgs.
Extended European Search Report dated Dec. 20, 2019 pertaining to European Patent Application No. 19188473.3.
Office Action dated Nov. 6, 2019 pertaining to Chinese Patent Application No. 201680035981.0.
Office Action dated Sep. 4, 2019 pertaining to U.S. Appl. No. 15/181,923, filed Jun. 14, 2016, 13 pgs.
Office Action dated May 10, 2019 pertaining to U.S. Appl. No. 15/181,923, filed Jun. 14, 2016, 16 pgs.
Office Action dated Dec. 13, 2018 pertaining to U.S. Appl. No. 15/181,923, filed Jun. 14, 2016.
International Search Report and Written Opinion pertaining to International Application No. PCT/US2018/051514 dated Jan. 3, 2019, 12 pages.
Pietrzykowski et al., Inorganic Chi mica Acta, 334, 385-394 (Year: 2002).
Non-Final Office Action pertaining to U.S. Appl. No. 15/830,800 dated Oct. 19, 2018.
P.D. Smith et al., "Ethylene dimerization over supported titanium alkoxides" Journal of Catalysis 105, pp. 187-198, 1987.
Al-Jaralla et al., "Part 1—Dimerization of Ethylene to Butene-1", Catalysis Today 14, pp. 1-124, 1992.
A. Hennico et al., "Butene-1 is made from ethylene", Hydrocarbon Processing, vol. 69:3 (1990)—Abstract Only.
International Search Report and Written Opinion dated Feb. 20, 2018 pertaining to International application No. PCT/US2017/064841.
International Search Report and Written Opinion pertaining to PCT/US2017/012299 dated Jun. 8, 2017.
Obrey et al., "A Lewis Base Promoted Alkyl/Alkoxide Ligand Redistribution: Reaction of [Me2Al{μ-OCPh3)]2 with THF", Organometallics, Nov. 1, 2001, vol. 20, No. 24, pp. 5119-5124.
T. Mole, "Organoaluminium Compounds—XI. Reaction of Trialkylaluminiums with Dialkylaluminium Alkoxides", Australian Journal of Chemistry, Jan. 1, 1966, pp. 381-386.
Forestiere et al., "Oligomerization of Monoolefins by Homogenous Catalysts", Oil & Gas Science and Technology, 2009, vol. 64, No. 6, pp. 649-667, Institut francais due petrole.
Invitation to Pay Additional Search Fees and Partial Search Report dated Sep. 15, 2016 for PCT Application No. PCT/US2016/037366 entitled "Antifouling Oligomerization Catalyst Systems".
International Search Report pertaining to PCT/US2016/037366 dated Nov. 21, 2016.
Written Opinion pertaining to PCT/US2016/037366 dated Nov. 21, 2016.
U.S. Office Action dated Mar. 22, 2022 pertaining to U.S. Appl. No. 16/935,842, filed Jul. 22, 2020, 36 pages.
U.S. Office Action dated Sep. 22, 2022 pertaining to U.S. Appl. No. 17/383,669, filed Jul. 23, 2021, pp. 1-23.

* cited by examiner

ANTIFOULING OLIGOMERIZATION CATALYST SYSTEMS

CROSS-REFERENCE TO RELATED APPLICATIONS

This application claims priority to U.S. Non-Provisional patent application Ser. No. 15/393,865 filed Dec. 29, 2016, which claims priority to U.S. Provisional Patent Application No. 62/275,932 filed Jan. 7, 2016, which is incorporated into this disclosure by reference in its entirety.

BACKGROUND

Field

Embodiments of the present disclosure generally relate to catalyst systems used in ethylene oligomerization and, more specifically, relate to antifouling catalyst systems used in ethylene oligomerization which reduce undesired polymerization.

Technical Background 1-butene and 1-hexene are important petrochemicals, especially for the productions of polyethylene. The reaction of ethylene and other alpha-olefins, especially 1-butene and 1-hexene, forms various grades of linear low density polyethylene (LLDPE), a useful commercial polymer. A source of 1-butene is the butene fraction from the effluent of a hydrocarbon cracker, such as a steam cracker or fluidized catalytic cracker. However, the process for recovering 1-butene from such an effluent requires several difficult process steps that may make the process undesirable.

Several commercial processes selectively oligomerize ethylene into alpha olefins such as 1-butene and 1-hexene. A commercially successful dimerization process is the Alphabutol™ Process, developed by the Institute Francais du Petrole (IFP), described in A. Forestiere, et al., "Oligomerization of Monoolefins by Homogenous Catalysts", Oil & Science and Technology—Review de l'Institute Francais du Petrole, pages 663-664 (Volume 64, Number 6, November 2009). This process uses a bubble-point reactor that contains 1-butene as a process fluid to oligomerize ethylene selectively into 1-butene.

There is a known problem with oligomerization systems: polymer formation. Long residence times and poor heat removal from the highly exothermic reactions lead to the formation of polyethylene-based residues. A side effect of chronic fouling is increasingly frequent process shutdowns and higher maintenance costs for removing adhered polymer residues. Polymer residues may build layer upon layer and eventually close off openings and ports in locations with fluid flow. Additionally, a polymer coating along the wall of a reactor may act as an insulator, which may negatively affect heat transfer to the reactor system. Polymer can also collect debris that can be catalytically active or that can poison the reaction process.

An especially troublesome issue is the formation of "hot spots". A hot spot is an area where external cooling is ineffective and catalyst activity is high. It represents a loss of process control. A hot spot can be an area of collected polymer that includes catalytically active material that fosters side-reactions, including polymerization. If left unchecked, the hot spot can eventually lead to a process shutdown due to the loss of cooling capacity, a runaway polymerization reaction, or both.

SUMMARY

There is a continual need for effective methods to prevent polymeric fouling on reactor system walls and tubes while maintaining the desired oligomerization rate and selectivity to form reaction product.

According to one embodiment, a catalyst system that reduces polymeric fouling may comprise at least one titanate compound, at least one aluminum compound, and at least one antifouling agent or a derivative thereof. The antifouling agent may comprise a structure comprising a central aluminum molecule bound to an R1 group, bound to an R2 group, and bound to an R3 group. One or more of the chemical groups R1, R2, and R3 may be antifouling groups comprising the structure $-O((CH_2)_nO)_mR4$, where n is an integer from 1 to 20, m is an integer from 1 to 100, and R4 is a hydrocarbyl group. The chemical groups R1, R2, or R3 that do not comprise the antifouling group, if any, may be hydrocarbyl groups.

According to another embodiment, 1-butene may be produced by a process comprising contacting ethylene with a catalyst system to oligomerize the ethylene to form 1-butene. The catalyst system may comprise at least one titanate compound, at least one aluminum compound, and at least one antifouling agent or a derivative thereof. The antifouling agent may comprise a structure comprising a central aluminum molecule bound to an R1 group, bound to an R2 group, and bound to an R3 group. One or more of the chemical groups R1, R2, and R3 may be antifouling groups comprising the structure $-O((CH_2)_nO)_mR4$, where n is an integer from 1 to 20, m is an integer from 1 to 100, and R4 is a hydrocarbyl group. The chemical groups R1, R2, or R3 that do not comprise the antifouling group, if any, may be hydrocarbyl groups.

Additional features and advantages of the embodiments described herein will be set forth in the detailed description which follows, and in part will be readily apparent to those skilled in the art from that description or recognized by practicing the embodiments described, including the detailed description which subsequently follows, and the claims.

DETAILED DESCRIPTION

One or more embodiments of the present disclosure are directed to catalyst systems which may be utilized in promoting ethylene oligomerization, such as the dimerization of ethylene to form 1-butene, while reducing reactor fouling caused by undesired polymerization. These catalyst systems are sometimes referred to in this disclosure as "antifouling ethylene oligomerization catalyst systems" or "antifouling catalyst systems". The antifouling catalyst systems described may comprise at least one titanate compound, at least one aluminum compound, and at least one antifouling agent or dimer thereof. The antifouling catalyst systems may further comprise one or more ether compounds. The antifouling catalyst systems may be used to selectively oligomerize ethylene to produce 1-butene, while reducing undesirable polymerization, sometimes referred to in this disclosure as "fouling". For example, reactor fouling may occur due to the formation of solid polyethylene-based residues which may reduce fluid flow and fully block or at least partially block fluids in a reactor system from flowing at a desired rate. It should be understood that the "antifouling ethylene oligomerization catalyst systems" or "antifouling catalyst systems" described may not completely eliminate fouling during a reaction. However, these catalyst systems reduce fouling as compared with catalyst systems which do not include an antifouling agent as described in the present disclosure. Also, it should be understood that while the catalyst systems of the present disclosure may be useful in ethylene oligomerization reactions, such as ethylene dimerization to form 1-butene, they may also be useful for the catalysis of other chemical reaction, and the antifouling catalyst systems described in this disclosure should not be considered limited in their use to the dimerization of ethylene to 1-butene.

As described previously in this disclosure, embodiments of the described antifouling catalyst systems may comprise one or more titanate compounds. While several titanate compounds may be included in the antifouling catalyst system, in some embodiments a single titanate compound may be included in the antifouling catalyst system. In one or more embodiments, the titanate compound may be an alkyl titanate. An alkyl titanate may have the structure $Ti(OR)_4$ in which R is a branched or straight chain alkyl group. In one or more embodiments, each alkyl group may comprise from 2 to 8 carbons, where each R group may be the same or different. Suitable alkyl titanates may include tetraethyl titanate, tetraisopropyl titanate, tetra-n-butyl titanate (sometimes referred to as titanium butoxide or tetrabutyl orthotitanate), 2-tetraethylhexyl titanate. In one or more embodiments, the titanate compound of the antifouling catalyst system consists of tetra-n-butyl titanate.

As also described previously in this disclosure, embodiments of the described antifouling catalyst systems may comprise one or more aluminum compounds. While several aluminum compounds may be included in the antifouling catalyst system, in some embodiments a single aluminum compound may be included. In one or more embodiments, one or more aluminum alkyl compounds may be included in the antifouling catalyst system. Aluminum alkyl compounds may have a structure of $AlR'_3$ or $AlR'_2H$, where R' is a straight chain or branched alkane comprising from 1 to 20 carbons, or an aluminoxane structure (that is, a partial hydrolysate of trialkylaluminum compounds). For example, and not by way of limitation, suitable aluminum alkyl compounds may include triethylaluminum, tripropylaluminum, tri-iso-butylaluminum, and trihexylaluminum. In one or more embodiments, the aluminum compound of the antifouling catalyst system consists of triethylaluminum.

The antifouling catalyst systems may comprise one or more antifouling agents or derivatives thereof. As used herein, a derivative refers to a derivative structure of an antifouling agent, such as a dimer, trimer, oligomer, polymer, isomer, hydrolysate of an antifouling agent described in this disclosure. In one or more embodiments, an antifouling agent may comprise a central aluminum molecule bonded to all three of a first chemical group R1, a second chemical group R2, and a third chemical group R3. Chemical Structure #1 depicts a generalized chemical structure of an antifouling agent.

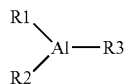

Chemical Structure #1—Generalized Antifouling Agent

In one or more embodiments, one or more of R1, R2, and R3 are antifouling groups comprising the structure —O((CH$_2$)$_n$O)$_m$R4, where n is an integer from 1 to 20 (for example, 1 to 15, 1 to 10, 1 to 5, 1 to 4, 1 to 3, 1 to 2, 2 to 20, 3 to 20, 4 to 20, 5 to 20, 10 to 20, or 15 to 20), m is an integer from 1 to 100 (for example, 1 to 10, 1 to 20, 1 to 30, 1 to 40, 1 to 50, 1 to 75, 5 to 100, 10 to 100, 25 to 100, 50 to 100, or 75 to 100), and R4 is a hydrocarbyl group. The structure of the antifouling group, —O((CH$_2$)$_n$O)$_m$R4, is depicted in Chemical Structure #2. The central aluminum atom is bonded to a terminal oxygen of the antifouling group opposite of the R4 hydrocarbyl group. As used throughout this disclosure, a hydrocarbyl group refers to a chemical group that consists of hydrogen and carbon atoms. For example, a hydrocarbyl group may be branched or unbranched, and may comprise one or more alkane moieties, one or more alkene moieties, one or more alkyne moieties, or combinations thereof. Hydrocarbyl groups may include cyclic or aromatic moieties. In one or more embodiments, R4 may be a hydrocarbyl group having from 1 to 100 carbon atoms, such as from 5 to 50 carbon atoms, or from 12 to 28 carbon atoms.

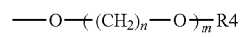

Chemical Structure #2—Antifouling Group

As previously described in this disclosure, one, two, or all three of R1, R2, and R3 may comprise the antifouling groups comprising the structure of Chemical Structure #2. In embodiments described in this disclosure, the chemical groups R1, R2, or R3 that do not comprise the antifouling group, if any, are hydrocarbyl groups. For example, R1 may be an antifouling group with the structure depicted in Chemical Structure #2 and R2 and R3 may be hydrocarbyl groups. In another embodiment, R1 and R2 may be antifouling groups with the structure depicted in Chemical Structure #2, and R3 may be a hydrocarbyl group. In another embodiment, R1, R2, and R3 may be antifouling groups with the structure depicted in Chemical Structure #2. When at least two of R1, R2, and R3 are hydrocarbyl groups, they may be identical to one another or may be different hydrocarbyl groups. Also, when two or more of R1, R2, or R3 are antifouling groups, the antifouling groups may be identical or chemically different. However, they will each have the generic structure depicted in Chemical Structure #2. R1, R2 and R3 that are hydrocarbyl groups may each have from 1 to 100 carbon atoms, such as, for example, from 1 to 50 carbon atoms. For example, if R1, R2, or R3 are hydrocarbyl groups, they may be straight chained alkanes such as methyl, ethyl, propyl, or butyl groups.

By way of example, if R1 is an antifouling group, and R2 and R3 are hydrocarbyl groups, the generalized structure of the antifouling agent can be represented by Chemical Structure #3.

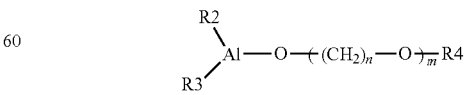

Chemical Structure #3—Example of Generalized Antifouling Agent

In one or more embodiments, the antifouling agent may comprise an R1 group that is an ethyl group, an R2 group that is an ethyl group, and an R3 that is an antifouling group having the structure —O((CH$_2$)$_n$O)$_m$R4, where n=2, m=4, and R4 is a dodeyl group. Such an antifouling agent can be written as (CH$_3$CH$_2$)$_2$AlO(CH$_2$CH$_2$O)$_4$(CH$_2$)$_{11}$CH$_3$, and has the chemical structure depicted in Chemical Structure #4, where "Et" represents an ethyl group.

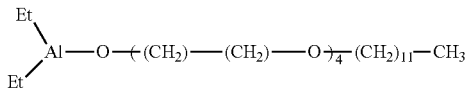

Chemical Structure #4—Example of Antifouling Agent

In one or more embodiments, the antifouling agent may be present as a dimerized form, referred to herein as an example of a derivative of an antifouling agent. A prepared antifouling agent may be present in both dimerized and non-dimerized (that is, non-bonded) form. For example, in a dimerized state, the antifouling agent may comprise a structure as shown in Chemical Structure #5. Chemical Structure #5 shows the dimerized embodiment of the antifouling agent structure depicted in Chemical Structure #3. In a dimerized embodiment, a bond may form between a central aluminum atom of an antifouling agent molecule and an oxygen atom of a neighboring antifouling agent molecule. It should be understood that while in Chemical Structures #5 the central aluminum atoms are bonded to the oxygen atom in the neighboring antifouling agent that is most near to its central aluminum atom, in other embodiments, this may not be the case, and the a central aluminum atom may bond with an oxygen atom of a neighboring antifouling agent which is not most near to its central aluminum atom.

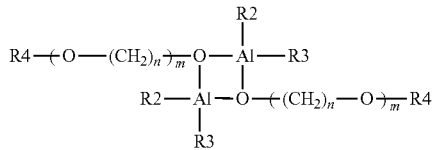

Chemical Structure #5—Example of Dimerized Antifouling Agent

In one or more embodiments, the antifouling agent may be present in different isomer states, one such example depicted in Chemical Structure #6. An isomer is an example of a derivative structure of an antifouling agent. For example, and as depicted in Chemical Structure #6, the central aluminum atom of an antifouling agent may be bonded to two oxygens atoms of a single antifouling group. It should be understood that while Chemical Structure #6 depicts an isomer where the two oxygen atoms most near to the central aluminum atom are bonded with the central aluminum atom, in other embodiments other isomers may form, such as an isomer formed when the central aluminum atom forms a bond with an oxygen atom which is not as close as another oxygen atom to the central aluminum atom in the antifouling agent molecule. For example, while Chemical Structure #6 shows a ring structure with 2 oxygen atoms and n carbon atoms, larger ring structures may form in other isomers, such as rings having three or more oxygen atoms. It should be understood that isomers of the antifouling agents described, such as that shown in Chemical Structure #6, are considered antifouling agents and fit into the base structure depicted in Chemical Structure #1. For instance, the existence of two oxygen atoms bonded to the central aluminum, where both oxygen atoms are part of an antifouling group, is considered to conform to the base structure depicted in Chemical Structure #1.

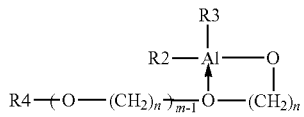

Chemical Structure #6—Example of Isomer of Antifouling Agent

In one or more embodiments, the antifouling catalyst systems may comprise more than one molecular species of antifouling agent. For example, the antifouling catalyst system may comprise antifouling agents with a varying number of antifouling groups. For example, some antifouling agent molecules may comprise none, one, two or three antifouling groups, while others comprise a different number of antifouling groups. The mixture of these antifouling agent species may form a bulk antifouling agent which can be characterized by its bulk molar ratio of hydrocarbyl groups to antifouling groups which are attached to the central aluminum atoms, respectively. For example, if half of the antifouling agent has one antifouling group and two hydrocarbyl groups, and, the other half of the antifouling agent has two antifouling groups and one hydrocarbyl group, then the bulk molar ratio of hydrocarbyl groups to antifouling groups would be 1:1 because there is a bulk equal amount of hydrocarbyl groups to antifouling groups. In one or more embodiments, the bulk molar ratio of hydrocarbyl groups to antifouling groups may be from be from 1:1 to 20:1. Non-limiting examples of bulk molar ratios of hydrocarbyl groups to antifouling groups include from 1:1 to 2:1, from 1:1 to 3:1, from 1:1 to 4:1, from 1:1 to 5:1, from 1:1 to 10:1, from 1:1 to 15:1, from 2:1 to 20:1, from 3:1 to 20:1, from 4:1 to 20:1, from 5:1 to 20:1, from 10:1 to 20:1, or from 15:1 to 20:1. According to one or more embodiments, the bulk molar ratio of hydrocarbyl groups to antifouling groups is from 1.5 to 2.5, from 1.8 to 2.2, or 2.

In one or more embodiments, the antifouling catalyst system may comprise one or more ether compounds. The one or more ether compounds may include cyclic ethers such as, but not limited to, tetrahydrofuran (THF), a dioxane, a Tetrahydropyran (THP), or combinations thereof.

The antifouling catalyst systems may comprise at least one or more titanate compounds, one or more aluminum compounds, and one or more antifouling agents. In one or more embodiments, the molar ratio of total titanate compound to total aluminum compound may be from 1:10 to 1:1.5 (such as, for example, from 1:10 to 1:2, from 1:10 to 1:3, from 1:10 to 1:4, from 1:10 to 1:5, from 1:10 to 1:6, from 1:10 to 1:7, from 1:10 to 1:8, from 1:10 to 1:9, from 1:9 to 1:1.5, from 1:8 to 1:1.5, from 1:7 to 1:1.5, from 1:6 to 1:1.5, from 1:5 to 1:1.5, from 1:4 to 1:1.5, from 1:3 to 1:1.5, or from 1:2 to 1.5).

In one or more embodiments, the molar ratio of total titanate compounds to total antifouling agent may be from 1:5 to 1:0.01 (such as, for example, from 1:5 to 1:0.05, from 1:5 to 1:0.1, from 1:5 to 1:0.3, from 1:5 to 1:0.5, from 1:5 to 1:0.7, from 1:5 to 1:1, from 1:5 to 1:2, from 1:5 to 1:3, from 1:5 to 1:4, from 1:4 to 1:0.01, from 1:3 to 1:0.01, from 1:2 to 1:0.01, from 1:1 to 1:0.01, from 1:0.7 to 1:0.01, or from 1:0.3 to 1:0.01).

In one or more embodiments, the molar ratio of total titanate compounds to total ether compounds may be from 1:20 to 1:0 (such as, for example, from 1:15 to 1:0, from 1:10 to 1:0, from 1:5 to 1:0, from 1:1 to 1:0, from 1:0.5 to 1:0, from 1:0.3 to 1:0, from 1:0.1 to 1:0, from 1:20 to 1:0.1, from 1:20 to 1:0.5, from 1:20 to 1:1, from 1:20 to 1:5, from 1:20 to 1:10).

It should be understood that the molar ratios of components of the antifouling catalyst systems described previously are representative of the total amount of each component of the antifouling catalyst system relative to the total amount of titanate compound, where the "total" amount refers to the molar amount of all species of the antifouling catalyst system which may be considered as a particular component type (that is, titanate compound, aluminum compound, ether compound, or antifouling agent). The total amount of a component may include two or more chemical species which are titanate compounds, aluminum compounds, ether compounds, or antifouling agents, respectively. It should also be understood that, as used in this disclosure, the total amount of aluminum compound does not include molecules that are considered as antifouling agents. Therefore, any species that is considered an antifouling agent as described in this disclosure does not contribute towards the total amount of aluminum compound even though the antifouling agent includes an aluminum central atom and may otherwise be considered as an aluminum-containing compound.

In one or more embodiments, the antifouling agent does not dealkylate, or is resistant to dealkylation as compared with other catalyst systems. Ethane releasing reactions may be undesirable, as they can contaminate a feed stream. In one or more embodiments, the antifouling agent does not deactivate the catalytic centers of one or more of the titanate compound or the aluminum compound.

According to another embodiment of the present disclosure, 1-butene may be produced. According to the method for 1-butene production, ethylene may be contacted with the antifouling catalyst system described previously to oligomerize the ethylene to form 1-butene. In one or more embodiments, the ethylene and antifouling catalyst system are supplied to a reactor and mixed. The reaction may be performed as a batch reaction or as a continuous process reaction, such as a continuous stir tank reactor process. According to embodiments, the pressure of the reactor may be from 5 bar to 100 bar, the reactor temperature may be from 30 degrees Celsius (° C.) to 180° C. However process conditions outside of these ranges are contemplated, especially in view of the specific design of the reactor system and concentrations of the reactants and catalysts.

Examples

The various embodiments of antifouling catalyst systems will be further clarified by the following examples. The examples are illustrative in nature, and should not be understood to limit the subject matter of the present disclosure.

To form an antifouling agent having the chemical structure $(CH_3CH_2)_2AlO(CH_2CH_2O)_4C_{12}H_{25}$ (shown as Chemical Structure #4), 10 milliliters (mL) of triethyl aluminum (1 molar (M) in hexane) was reacted with 10 mL of polyethylene glycol dodecyl ether (1 M in hexane). Specifically, polyethylene glycol dodecyl ether was first dried with anhydrous grade sodium sulfate to remove any residual moisture. The dried polyethylene dodecyl ether was then added dropwise to the triethyl aluminum in a 30 mL flask. The reaction mixture was subsequently stirred for 15 minutes. The reaction was carried out in an inert atmosphere inside a glove box. Light color change and release of ethane gas were observed during the reaction. Other antifouling agents were produced though similar techniques which incorporated reactants suitable to achieve antifouling agents having varying values of n, m, and R4 as described in this disclosure with reference to antifouling groups.

To evaluate the anti-fouling effects of the antifouling catalyst systems described, ethylene oligomerization reactions were carried out and evaluated. Multiple sample antifouling catalyst systems were formulated. Detailed structure of the antifouling agents used, as well as ratios of are listed in Table 1, For the experiments, catalyst mixtures were used that contained titanium tetrabutoxide (denoted as "Ti" in Table 1), THF, triethyl aluminum (denoted as "TEAL" in Table 1), and antifouling agents (denoted as "AFA" in Table 1). The antifouling agents utilized are described previously in this disclosure and are depicted in Chemical Structure #3 (where for the experiments, R2 and R3 are ethyl groups, and n, m, and R4 are specified in Table 1). In addition to the catalyst mixtures containing antifouling agent, comparative examples which did not contain antifouling agent were tested and compared with the catalyst systems which included antifouling agents.

The components of the sample catalyst systems were prepared and transferred into metal charging cylinders in a glove box. The THF was premixed with the titanium tetrabutoxide (in samples where TI-IF was included) and transferred to a charging cylinder, and the antifouling agent was premixed with the triethyl aluminum in heptane (1 M) utilized as a solvent. The oligomerization reactions were conducted in an autoclave batch reactor unit (1000 mL, volume). In a typical reaction run, the reactor vessel was vacuum purged with ultrapure nitrogen to remove oxygen and moisture. Then, the batch reactor was filled with anhydrous hexane and kept at 50° C. The anti-fouling agent and triethyl aluminum solution in heptane (1M) was then introduced into the reaction vessel. Then, the pre-mixed solution containing titanium tetrabutoxide and THF was introduced into the reactor. The catalyst solution had a concentration of titanium tetrabutoxide of 1 micromolar. Following introduction of the components of the catalyst system, the reactor was pressurized to 2.3 mega-Pascals (MPa) with ethylene and the temperature of the reactor was set to 53° C. with a stirring rate of 300 rpm. The dimerization reaction was terminated by injecting 2 mL, of ethanol after 30 minutes. The reactor was subsequently depressurized. The remaining solid polymer was filtered, dried overnight in an oven at 110° C. and weighed.

Table 1 shows the dimerization activity and weight of polymer deposit for reactions which utilized each of the sample catalyst systems. As is evident by the reaction data of Table 1, the addition of the antifouling additive greatly reduced polymer formation.

TABLE 1

| | Molar Ratio of Ti:THF:TEAL:AFA | n | m | R4 | Activity (grams of ethylene per hour per millimoles of titanium) | Polymer Produced (mg) |
|---|---|---|---|---|---|---|
| Comparative Example 1 | 1:4:7.5:0 | N/A | N/A | N/A | 221 | 200 |
| Example 1 | 1:4:7:0.4 | 2 | 4 | $C_{12}H_{25}$-n | 291 | 35 |
| Example 2 | 1:4:7.5:3 | 2 | 10 | $C_{18}H_{37}$-n | 224 | 21 |
| Example 3 | 1:4:7.5:3 | 2 | 20 | $C_{18}H_{37}$-n | 228 | 78 |
| Comparative Example 2 | 1:6:7.5:0 | N/A | N/A | N/A | 190 | 187 |
| Example 4 | 1:6:7.5:0.6 | 2 | 4 | $C_{12}H_{25}$-n | 254 | N/A |
| Comparative Example 3 | 1:6:7.5:0 | N/A | N/A | N/A | 278 | 91 |
| Example 5 | 1:6:7.5:0.6 | 2 | 2 | $C_{18}H_{37}$-n | 276 | 4 |
| Example 6 | 1:6:7.5:0.6 | 2 | 4 | $C_{12}H_{25}$-n | 289 | 6 |
| Example 7 | 1:6:7.5:1 | 2 | 4 | $C_{12}H_{25}$-n | 263 | 4 |

What is claimed is:

1. A catalyst system that reduces polymeric fouling, the catalyst system comprising:
   at least one titanate compound;
   at least one aluminum compound; and
   at least one antifouling agent or a dimer, trimer, oligomer, polymer, or isomer, where the antifouling agent comprises the structure:

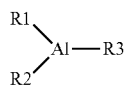

where R1, R2, and R3 are antifouling groups comprising the structure $—O((CH_2)_nO)_mR4$, where:
   n is an integer from 1 to 20;
   m is an integer from 1 to 100; and
   R4 is a hydrocarbyl group.

2. The catalyst system of claim 1, where n is from 1 to 5.

3. The catalyst system of claim 1, where m is from 1 to 20.

4. The catalyst system of claim 1, where R4 has from 1 to 100 carbon atoms.

5. The catalyst system of claim 1, further comprising an ether compound.

6. The catalyst system of claim 5, where the ether compound is tetrahydrofuran, a dioxane, or tetrahydropyran.

7. The catalyst system of claim 1, where at least one of the titanate compounds is an alkyl titanate.

8. The catalyst system of claim 7, where the alkyl titanate has the structure $Ti(OR)_4$, where R is a branched or straight chain alkyl radical comprising from 2 to 8 carbon atoms.

9. The catalyst system of claim 7, where the alkyl titanate is chosen from tetraethyl titanate, tetraisopropyl titanate, tetra-n-butyl titanate, or 2-tetraethylhexyl titanate.

10. The catalyst system of claim 1, where at least one of the aluminum compounds has the structure $AlR'_3$ or $AlR'_2H$, where R' is a branched or straight chain alkyl radical comprising from 2 to 8 carbon atoms.

11. The catalyst system of claim 1, where at least one of the aluminum compounds is chosen from triethylaluminum, tripropylaluminum, tri-iso-butylaluminum, trihexylaluminum, or an aluminoxane.

12. The catalyst system of claim 1, where a molar ratio of total titanate compound to total aluminum compound is from 1:10 to 1:1.5.

13. The catalyst system of claim 1, where a molar ratio of total titanate compound to total antifouling agent is from 1:5 to 1:0.01.

14. The catalyst system of claim 1, where a molar ratio of total titanate compound to total ether compound is from 1:10 to 1:0.

15. The catalyst system of claim 1, where the catalyst system comprises one or more of the at least one antifouling agent, the dimer of the antifouling agent, and the isomer of the antifouling agent.

16. The catalyst system of claim 1, where the catalyst system comprises one or more of the at least one antifouling agent and the dimer of the antifouling agent, wherein the dimer of the antifouling agent has the structure:

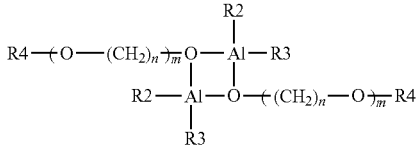

where R2, and R3 are antifouling groups comprising the structure $—O((CH_2)_nO)_mR4$, where:
   n is an integer from 1 to 20;
   m is an integer from 1 to 100; and
   R4 is a hydrocarbyl group.

17. A catalyst system that reduces polymeric fouling, the catalyst system comprising:
   at least one titanate compound;
   at least one aluminum compound;
   at least one ether compound; and
   at least one antifouling agent or a dimer, trimer, oligomer, polymer, or isomer, where the antifouling agent comprises the structure:

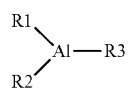

where R1, R2, and R3 are antifouling groups comprising the structure $-O((CH_2)_nO)_mR4$, where:
   n is an integer from 1 to 20;
   m is an integer from 1 to 100; and
   R4 is a hydrocarbyl group. a molar ratio of total titanate compound to total ether compound is from 1:10 to 1:0.

18. The catalyst system of claim 17, where at least one of the aluminum compounds has the structure $AlR'_3$ or $AlR'_2H$, where R' is a branched or straight chain alkyl radical comprising from 2 to 8 carbon atoms.

19. The catalyst system of claim 17, where a molar ratio of total titanate compound to total aluminum compound is from 1:10 to 1:1.5.

20. The catalyst system of claim 17, where a molar ratio of total titanate compound to total antifouling agent is from 1:5 to 1:0.01.

* * * * *